US00PP37248P2

(12) United States Plant Patent
Gerits

(10) Patent No.: US PP37,248 P2
(45) Date of Patent: Feb. 3, 2026

(54) ***ECHINACEA* PLANT NAMED 'PEECHPANRO'**

(50) Latin Name: *Echinacea purpurea*
Varietal Denomination: PEECHPANRO

(71) Applicant: Perennial Green GmbH, Kempen (DE)

(72) Inventor: Werner Gerits, Kempen (DE)

(73) Assignee: Perennial Green GMBH (DE)

( * ) Notice: Subject to any disclaimer, the term of this patent is extended or adjusted under 35 U.S.C. 154(b) by 0 days.

(21) Appl. No.: 18/911,584

(22) Filed: Oct. 10, 2024

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

(56) References Cited

U.S. PATENT DOCUMENTS

PP18,429 P2 * 1/2008 Oudolf ..... A01H 5/02
Plt./428

OTHER PUBLICATIONS https://online.plantvarieties.eu/publicSearch; Citation for 'Peechpanro'; CPVO Application Consultation Version4.23.10; 2025.*

* cited by examiner

*Primary Examiner* — Susan Mccormick Ewoldt

(57) ABSTRACT

A new and distinct cultivar of *Echinacea* plant named 'PEECHPANRO' is disclosed, characterized by plants with basal branching and bright purple-pink ray florets. Ray floret color continues to be vibrant when aging and fading. Plants have a long flowering period, from June to November. The new variety is an *Echinacea*, normally produced as an outdoor garden plant.

2 Drawing Sheets

Figure 1:
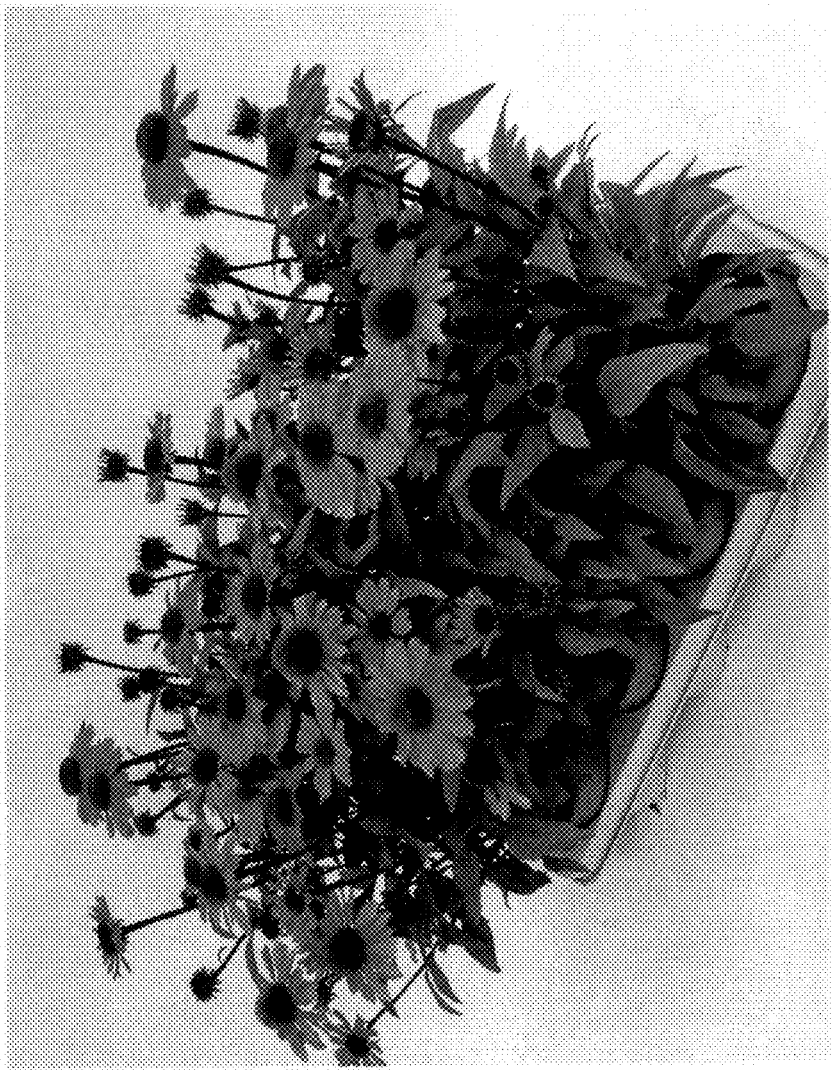

Latin name of the genus and species: *Echinacea purpurea.*

Variety denomination: 'PEECHPANRO'.

BACKGROUND OF THE INVENTION

The new *Echinacea* cultivar is a product of a planned breeding program conducted by the inventor in Wachtendonk, Germany. The crossing resulting in this new variety was made in July of 2020. The seed parent is the unpatented variety *Echinacea* 'EC20-82-2'. The pollen parent is the unpatented variety *Echinacea* 'EC20-82-5'.

The new variety was discovered in June of 2021 by the inventor at the same location in Wachtendonk, Germany. Asexual propagation of *Echinacea* was performed by vegetative cuttings in August of 2021, in Wachtendonk, Germany. After selection of 'PEECHPANRO', extensive confidential testing has been performed to determine and define the desirable characteristics of the new variety.

SUMMARY OF THE INVENTION

The cultivar 'PEECHPANRO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PEECHPANRO'. These characteristics in combination distinguish 'PEECHPANRO' as a new and distinct *Echinacea* cultivar:

1. Early and long blooming period (from June to November).

2. Basal branching.
3. Bright purple-pink ray floret color.
4. Keeps color at fading.
5. Propagation through vegetative cuttings.

PARENT COMPARISONS

Plants of 'PEECHPANRO' are similar in some horticultural characteristics to the seed parent. The new variety, however, differs in the following:

1. Ray floret color of the new variety is bright purple-pink, while ray floret color of the seed parent is a less vibrant purple-pink.
2. Inflorescences of the new variety have more ray florets than flowers of the seed parent.
3. Inflorescences of the new variety are larger than inflorescences of the seed parent.

Plants of 'PEECHPANRO' are similar in some horticultural characteristics to the pollen parent. The new variety, however, differs in the following:

1. Ray floret color of the new variety is bright purple-pink, while ray floret color of the pollen parent is light pink.
2. Plants of the new variety have basal branches, while plants of the pollen parent have no basal branches.

COMMERCIAL COMPARISONS

Plants of 'PEECHPANRO' are similar in some horticultural characteristics to the variety *Echinacea* 'Fatal Attraction', U.S. Plant Pat. No. 18,429. The new variety, however, differs in the following:

'PEECHPANRO' produces an average quantity of ray florets of 20; this comparator produces an average ray floret quantity of 36.

2. Stems of the new variety are thinner (2 mm) than stems of this comparator (5 mm).
3. Stem color of the new variety is (178B); stem color of this comparator is 187A.
4. Ray florets of the new variety are wider (12.5) than ray florets of this comparator (8 mm).
5. Plants of the new variety are shorter (40 cm) than plants of this comparator (57 cm).
6. 'PEECHPANRO' produces about 200 disc florets which are colored Greyed-Purple 187A at maturity; this comparator produces about 400 disc florets which are colored Greyed-Green 197A tinted 152A and 152B at maturity.

Plants of 'PEECHPANRO' are similar in some horticultural characteristics to the variety *Echinacea* 'Dark Pink Pearl', unpatented. The new variety, however, differs in the following:

1. Flower color of the new variety is purple-pink, while flower color of this comparator is salmon-pink.
2. Ray florets of the new variety are about 30% broader than ray florets of this comparator.
3. Blooming period of the new variety is longer than the blooming period of this comparator.
4 Plants of the new variety are shorter (40 cm) than plants (50 cm) of this comparator.
5. Plants of the new variety have more basal leaves and branches than plants of this comparator.

BRIEF DESCRIPTION OF THE PHOTOGRAPHS

The accompanying photograph in FIG. 1 illustrates in full color a typical plants of 'PEECHPANRO' approximately 4 months from a rooted cutting, grown in 12 cm pots.

Figure 2:
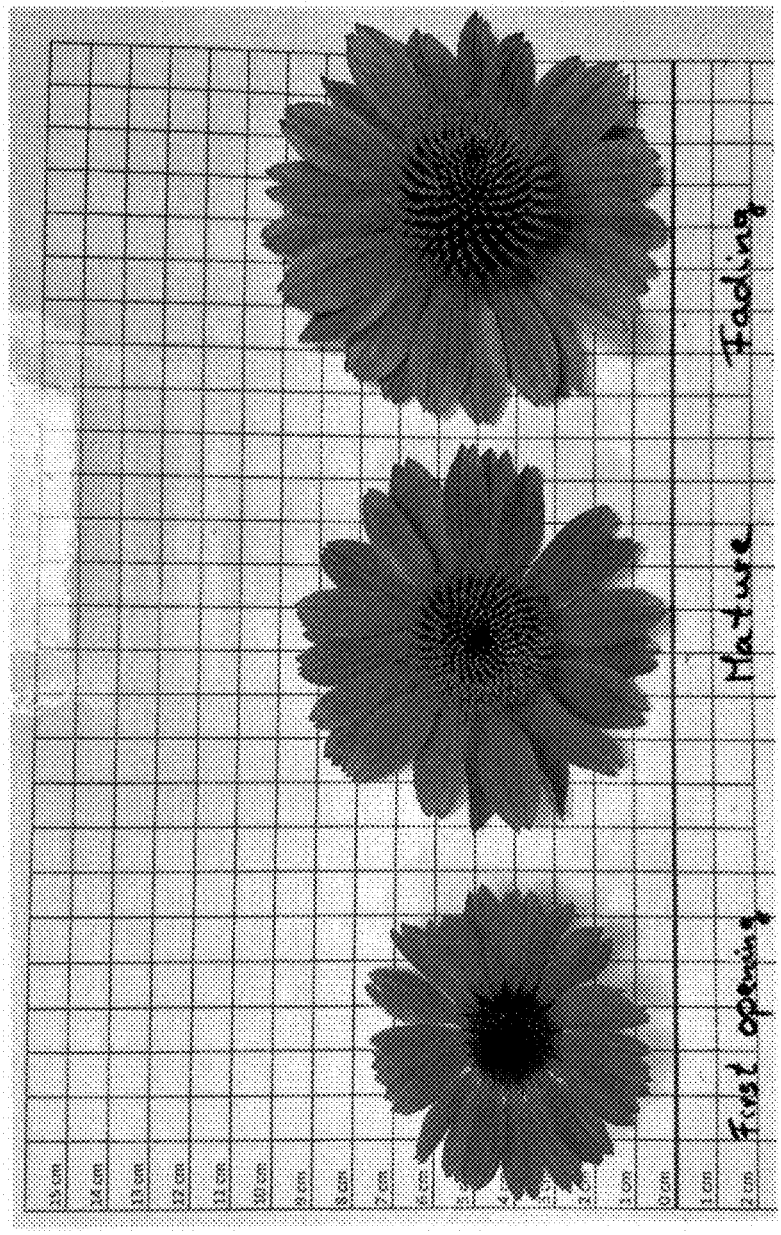

FIG. 2 illustrates maturity progression of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2015 except where general terms of ordinary dictionary significance are used. The following observations and measurements describe 'PEECHPANRO' plants grown in Kempen, Germany, under natural lighting. Measurements were taken August 2024. The growing temperature ranged from approximately 15° C. to 32° C. during the days, 8° C. to 20° C. during the nights. Measurements and numerical values represent averages of typical plant types.

Botanical classification: *Echinacea purpurea* 'PEECHPANRO'.

PROPAGATION

Propagation method: Vegetative cuttings.

Time to initiate rooting: 15 to 20 days at approximately 18° C. to 22° C.

Time to produce a rooted cutting: Approximately 12 weeks.

Root description: Fibrous and branched. Young roots colored white, older roots colored creamy-brown, not accurately measured by R.H.S. chart.

PLANT

Age of plant described: Approximately 5 months from a rooted cutting.

Growth habit: Hardy, upright, herbaceous perennial.

Height: Approximately 40 cm.

Plant spread: Approximately 35 cm.

Growth rate: Moderate.

Branching characteristics: Porrect, alternate.

Length of lateral branches: Approximately 20 cm.

Diameter of lateral branches: Approximately 0.2 cm.

Quantity of lateral branches: 2 to 3.

Characteristics of primary lateral branches:

*Aspect*.—Approximately 20° from base of plant (vertical).

*Color*.—Near RHS Reddish-Orange 178B.

*Texture*.—Hispid; hair color near RHS White NN155D.

Internode length: Approximately 5 cm.

FOLIAGE

Leaf:

*Arrangement*.—Alternate, simple.

*Attachment*.—Sessile, fused in lateral leaves, long petiole in basal leaves.

*Quantity*.—Approximately 4 per branch.

*Length*.—Smallest apical leaves, approximately 4.5 cm; largest basal leaves, approximately 9 cm.

*Width*.—Smallest apical leaves, approximately 1.4 cm; largest basal leaves, approximately 4.1 cm.

*Shape*.—Narrowly ovate to lanceolate.

*Apex*.—Acute.

*Base*.—Lateral leaves attenuate, fused to petiole; basal leaves cordate to attenuate, fused to petiole.

*Margin*.—Entire, finely serrate.

*Texture*.—Moderately hispid, both sides.

*Leaf internode length*.—Approximately 3.4 cm on stems. Basal leaves grow from ground level.

*Color*.—Young foliage upper side: Near RHS Green 137A. Young foliage under side: Near RHS Green 137C. Mature foliage upper side: Near RHS Green NN137A. Mature foliage under side: Near RHS Green 137C.

*Venation*.—Pattern: Pinnate. Color, upper side: Near RHS Yellow-Green 145C. Color, under side: Near RHS Yellow-Green 145C.

Petiole: Basal leaves only.

*Length*.—Approximately 12.5 cm.

*Diameter*.—Approximately 0.2 cm.

*Color*.—Near Green 137C both surfaces.

*Texture*.—Glabrous near base, becoming sparsely pubescent near leaf blade.

FLOWER

Natural flowering season: Naturally blooming June to November in Kempen, Germany.

Days to flowering from rooted cutting: 55 days.

Inflorescence and flower type and habit: Composite, single inflorescence held terminally on strong peduncle.

Quantity of inflorescences per lateral stem: 1.

Quantity of open inflorescences and buds per plant: Average 20.
Rate of opening: 3 to 5 days from bud to fully opened flower.
Flower longevity on plant: Approximately 20 days.
Persistent or self-cleaning: Persistent.
Fragrance: Faint, sweet.
Bud:
*Shape*.—Oblate globular.
*Length*.—Approximately 0.8 cm.
*Diameter*.—Approximately 1 cm.
*Color*.—Near RHS Greyed-Purple 187A.
Flower size:
*Diameter*.—Approximately 9 cm.
*Depth*.—Approximately 2.8 cm.
*Disc diameter*.—Approximately 2.9 cm.
*Receptacle shape*.—Conical.
*Receptacle height*.—Average 0.5 cm.
*Receptacle diameter*.—Average 1.6 cm.
Ray florets:
*Arrangement*.—Rotationally symmetric.
*Aspect/orientation*.—Perpendicular to disc (also in young and mature flower).
*Shape*.—Narrowly oblanceolate.
*Number*.—Average 20.
*Length*.—Approximately 3.4 cm.
*Width*.—Approximately 1.25 cm.
*Apex*.—Incised with two acute tips.
*Base*.—Attenuate.
*Margin*.—Entire.
*Texture*.—Smooth, ribbed longitudinally.
*Color*.—Upper surface at first opening: Near RHS Red-Purple 61B. Upper surface at maturity: Near RHS Red-Purple 64B. Upper surface at fading: Near RHS Red-Purple 64D flushed 63D. Under surface at first opening: Near RHS Red-Purple 70C. Under surface at maturity: Near RHS Red-Purple 59D. Under surface at fading: Near RHS Red-Purple 59D streaked with Yellow-Green 145B.
Disc florets:
*Arrangement*.—Spirally arranged in center of each inflorescence.
*Aspect/orientation*.—Perpendicular to disc (also in young and mature flower).
*Shape*.—Tubular.
*Number*.—Approximately 200.
*Length*.—Approximately 1 cm.
*Width*.—Approximately 2 mm.
*Apex*.—Five acute tips.
*Base*.—Fused into tube.
*Margin*.—Entire.
*Texture*.—Glabrous, glossy.
*Color*.—At first opening: Near RHS Yellow-Green 144B flushed with Greyed-Purple 183D. At maturity: Near RHS Greyed-Purple 187A.
*Receptacle spines*.—Number: 1 per disc floret. Spine shape: Cylindrical with conical tip. Spine apex: Acute. Spine texture: Glabrous, glossy. Spine apex color: Near RHS Greyed-Purple 183A. Spine mid-section color: Near RHS Orange N25A. Spine base color: Near RHS Yellow-Green 145A.
Phyllaries/involucral bracts:
*Arrangement*.—Three whorls.
*Number*.—Approximately 45.
*Length*.—Approximately 1 cm.
*Width*.—Approximately 0.25 cm.
*Shape*.—Narrowly ovate to lanceolate.
*Apex*.—Acute.
*Base*.—Truncate.
*Margin*.—Entire, hispid.
*Texture*.—Glabrous.
*Color*.—Inside: Near RHS Green 137B. Outside: Near RHS Green NN137B.
Peduncles:
*Length*.—Average 35 cm.
*Width*.—Average 0.35 cm.
*Texture*.—Moderately hispid.
*Color*.—Near RHS Greyed-Orange 175A combined with Yellow-Green 145A.

REPRODUCTIVE ORGANS

Androecium:
Stamens:
*Number*.—5 per disc floret.
*Filament length*.—Approximately 0.2 cm.
*Filament color*.—Near RHS Yellow-Green 145D.
Anthers:
*Shape*.—Oblong.
*Length*.—About 0.3 cm.
*Color*.—Near RHS Orange N167A.
*Pollen*.—Color: Near RHS Yellow 13A. Quantity: Abundant.
Gynoecium:
Pistil:
*Length*.—Approximately 0.6 cm.
*Style*.—Length: About 0.4 cm. Color: Near Yellow-Green 145C.
*Stigma*.—Shape: Decurrent. Color: Near RHS Red 187A. Ovary Color: Near Yellow-Green 145D.

SEEDS

Seed achene:
*Length*.—About 3 to 5 mm.
*Width*.—About 2 mm.
*Color*.—Near RHS Yellow-White 158C to Grey-Brown 199D.

OTHER CHARACTERISTICS

Fruit: Not observed.
Disease resistance: Neither resistance or susceptibility to normal diseases and pests of *Echinacea* has been observed.
Drought tolerance and temperature tolerance: Hardy perennial to −20° C. Upper temperature tolerance to at least 45° C. Some drought tolerance, established plants can tolerate infrequent summer waterings.

What is claimed is:

1. A new and distinct cultivar of *Echinacea* plant named 'PEECHPANRO' as herein illustrated and described.

* * * * *